United States Patent [19]

Yazawa et al.

[11] Patent Number: 4,912,215

[45] Date of Patent: Mar. 27, 1990

[54] Q-1047 SUBSTANCES

[75] Inventors: Hidenori Yazawa, Tokyo; Harumitsu Imai, Kanagawa; Kenichi Suzuki, Saitama; Shigenobu Kadota; Takeshi Saito, both of Tokyo, all of Japan

[73] Assignee: Yamanouchi Pharmaceutical Co., Ltd., Tokyo, Japan

[21] Appl. No.: 336,750

[22] Filed: Apr. 12, 1989

[51] Int. Cl.$^4$ ............... C07D 225/06; C12P 17/10
[52] U.S. Cl. ................................. 540/461; 435/121
[58] Field of Search ......................... 540/461

[56] References Cited

U.S. PATENT DOCUMENTS 4,421,687 12/1983 Hasegawa et al. ............... 540/461

Primary Examiner—Robert T. Bond
Attorney, Agent, or Firm—Burgess, Ryan and Wayne

[57] ABSTRACT

A Q-1047 substance of the general formula (I) and methods of producing the same, which has antioxidant activity and are useful as prophylactic and therapeutic agents for nephritis.

4 Claims, 18 Drawing Sheets

Q-1047 SUBSTANCES

FIELD OF THE INVENTION

This invention relates to Q-1047 substances which can eliminate active oxygen species in the living organism, can inhibit or reduce the formation of lipid peroxides, to methods of producing the same and to microorganisms capable of producing the same.

BACKGROUND OF THE INVENTION

To living organisms, oxygen is essential in supporting their life for example, in producing energy and in metabolism. Reactions in energy-producing systems, enzymatic reactions, and reactions induced by ultraviolet rays or radiations convert oxygen to he so-called active oxygen species, such as oxygen anion radical, peroxide ion and hydroxy radical. While the active oxygen species are of service to living organisms, promoting the function of oxygenase and the bactericidal activity of leukocytes, for instance, they promote the peroxidation of unsaturated fatty acids occurring abundantly in living organisms and constituting phospholipids in biomembranes, such as oleic acid, linolic acid, linolenic acid and arachidonic acid, causing formation of lipid peroxides. Like the above-mentioned active oxygen species, these lipid peroxides induce formation of alkoxy and hydroxy radicals, thus invading biomembranes and causing membrane disorders and deactivation of various enzymes [Taisha (Metabolism & Disease), 15 (10), special issue "Active Oxygen", 1978].

Enzymes capable of contributing metabolic deactivation of the above-mentioned active oxygen species, for example superoxide dismutases (SODs), catalase and glutathione peroxidase, vitamins having antioxidant activity, typically a-tocopherol (vitamin E), and the like are present in living organisms and their actions serve to keep the living organisms in a normal condition. However, it is not rare that, for one cause or another, the proper defense mechanisms in which such substances as mentioned above are involved become defective or the production of active oxygen species and the formation and accumulation of lipid peroxides occur to an extent that the capacity of the defense mechanisms is no more sufficient to deal the active oxygen species and/or lipid peroxides. In case some or other deficit is caused in the defense mechanisms in such a manner, peroxidation proceeds in the manner of chain reaction and causes various severe disorders in the living organisms. As typical examples of such disorders, there are mentioned various diseases due to platelet aggregation, inflammation, hepatopathy, arteriosclerosis, hemolysis, aging or senile diseases, retinopathy, pulmonary disorder, cardiopulmonary disorder due to certain drugs, and ischemic angiopathy [Jikken Igaku (Experimental Medicine), 4 (12), special issue for 1986 "Free radicals in living organisms and diseases"].

Drugs generally classifiable as antioxidants have been developed for the prevention and treatment of the above-mentioned diseases.

SUMMARY OF THE INVENTION

The invention now provides Q-1047 substances having the planar structural formula (I) shown below and methods of producing said substances.

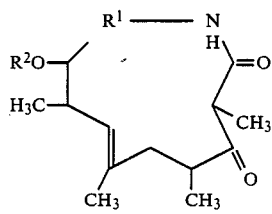

wherein $R^1$ is a group of the formula

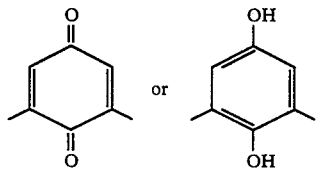

and $R^2$ is a hydrogen atom or a group of the formula

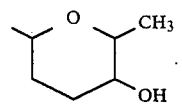

The compounds according to the invention have antioxidant activity and are useful as prophylactic and therapeutic agents for various diseases such as mentioned above.

BRIEF DESCRIPTION OF THE DRAWINGS

In the accompanying drawings.

DETAILED DESCRIPTION OF THE INVENTION

The Q-1047 substance of the above formula (I) includes four substances differing in the combination of $R^1$ and $R^2$ in the formula, and stereoisomers thereof.

Each Q-1047 substance contains a plurality of asymmetric carbon atoms and a double bond, hence includes stereoisomers due to such structural characteristics. The present invention covers all these isomers.

Typical examples of the compound (I) according to the invention that have been actually produced are as follows:

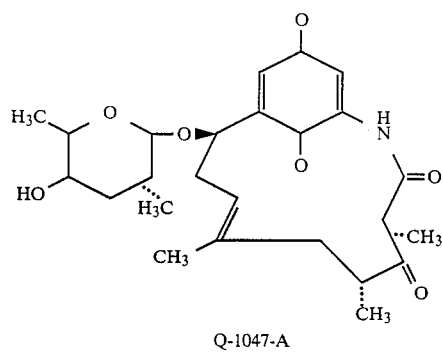

Q-1047-A

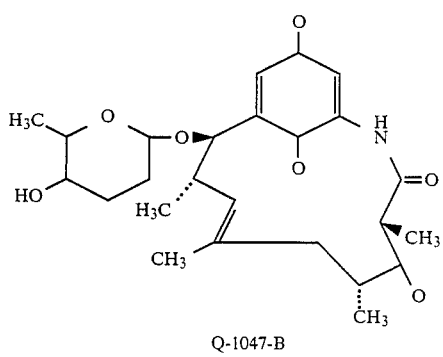

Q-1047-B

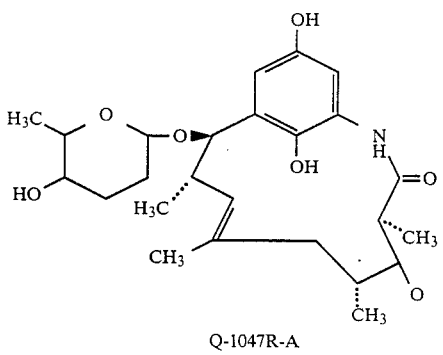

Q-1047R-A

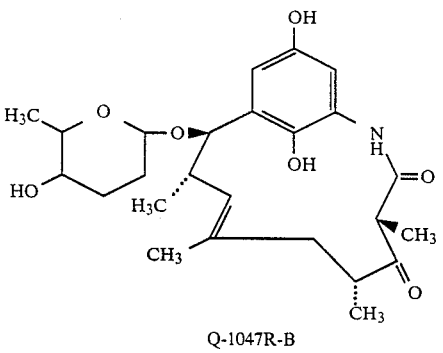

Q-1047R-B

-continued

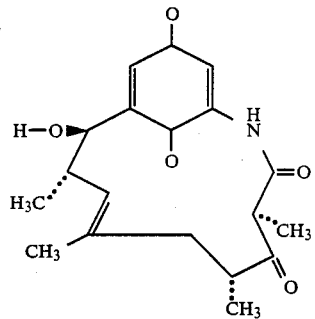

Q-1047H-A-A

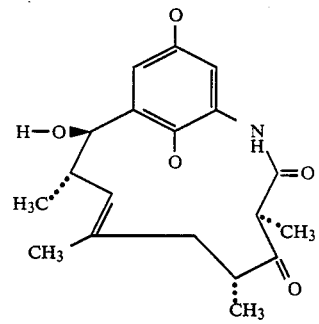

Q-1047H-R-A

The physiochemical characteristics of these compounds are summarized below in Table 1.

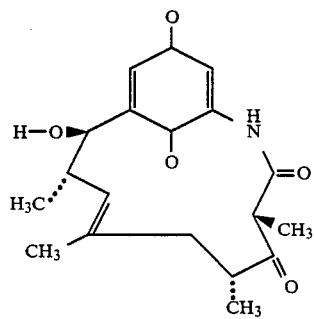

Q-1047H-A-B

TABLE 1-1

Figure 1:
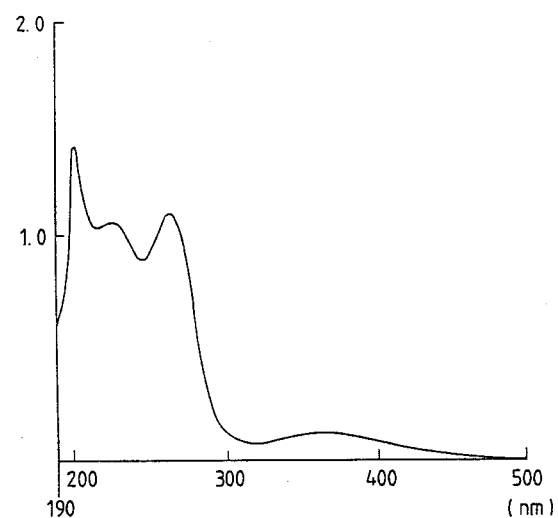
FIG. 1 shows an ultraviolet absorption spectrum of Q-1047-A substance.
Figure 2:
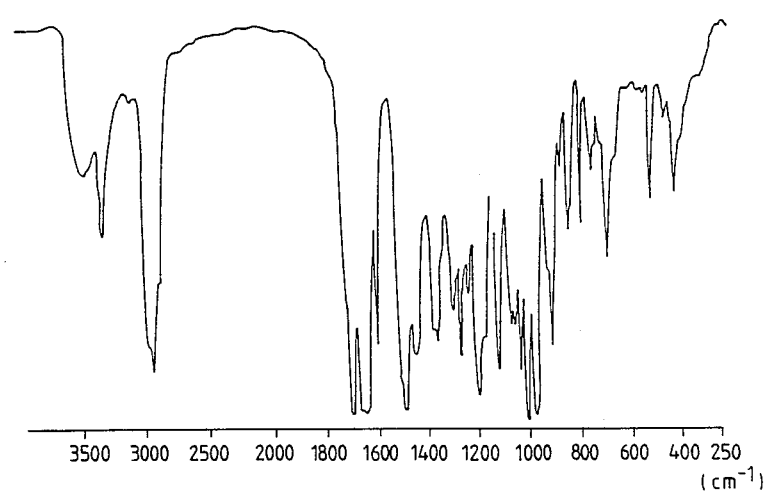
FIG. 2 shows an infrared absorption spectrum of Q-1047-A substance.
Figure 3:
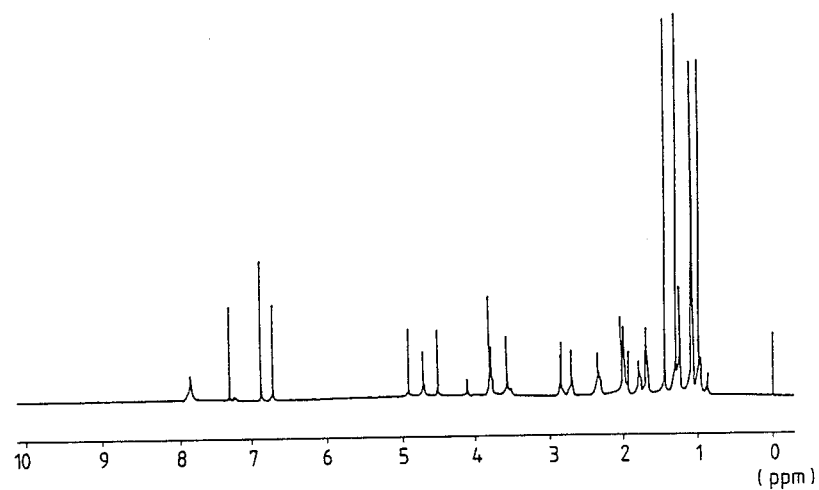
FIG. 3 shows a $^1$H-nuclear magnetic resonance spectrum of Q-1047-A substance.
Figure 4:
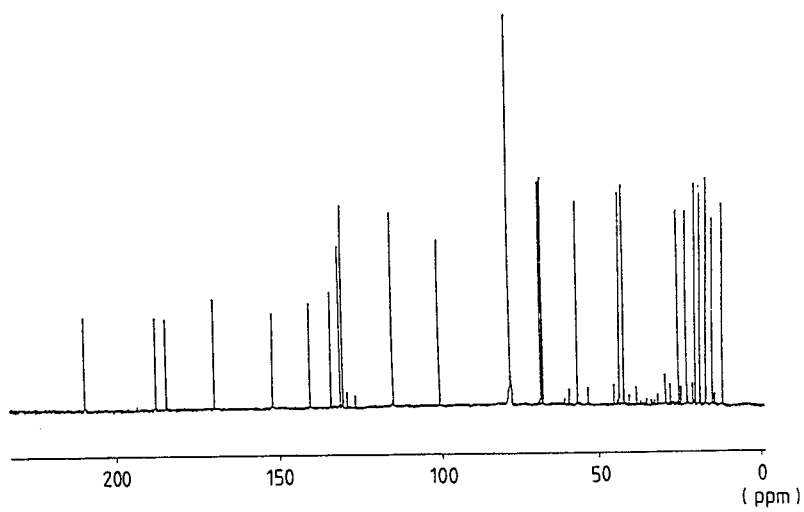
FIG. 4 shows a $^{13}$C nuclear magnetic resonance spectrum of Q-1047-A substance.
Figure 5:
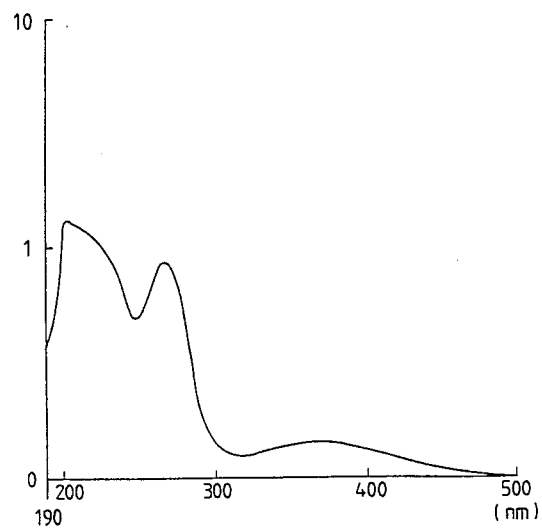
FIG. 5 shows an ultraviolet absorption spectrum of Q-1047-B substance.
Figure 6:
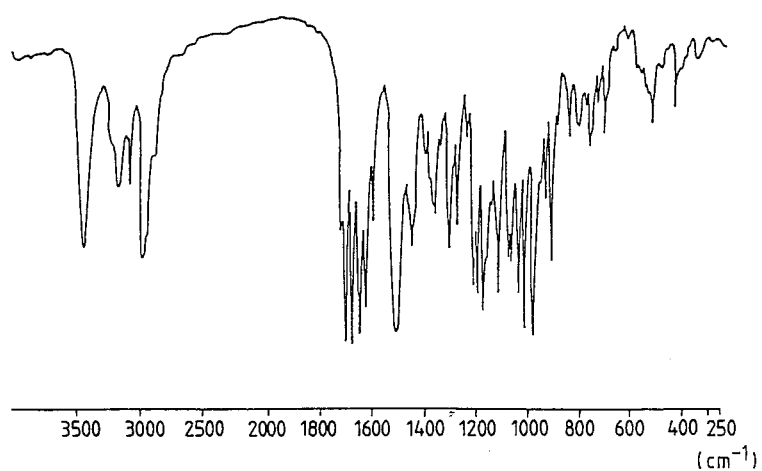
FIG. 6 shows an infrared absorption spectrum of Q-1047-B substance.
Figure 7:
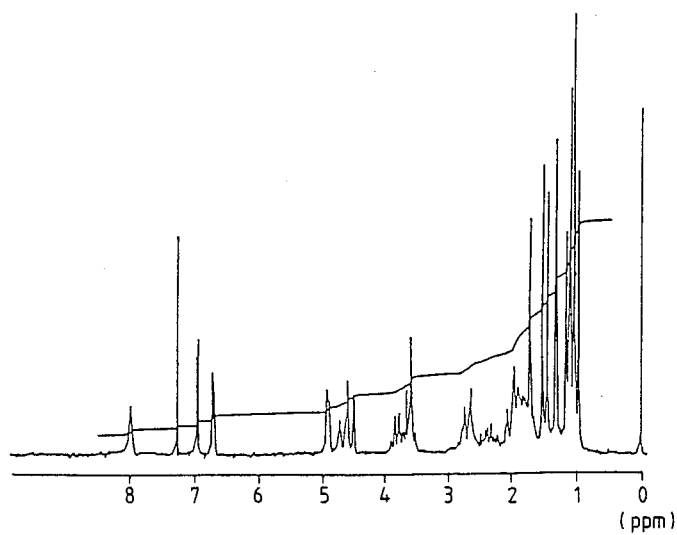
FIG. 7 shows a $^1$H-nuclear magnetic resonance spectrum of Q-1047-B substance.
Figure 8:
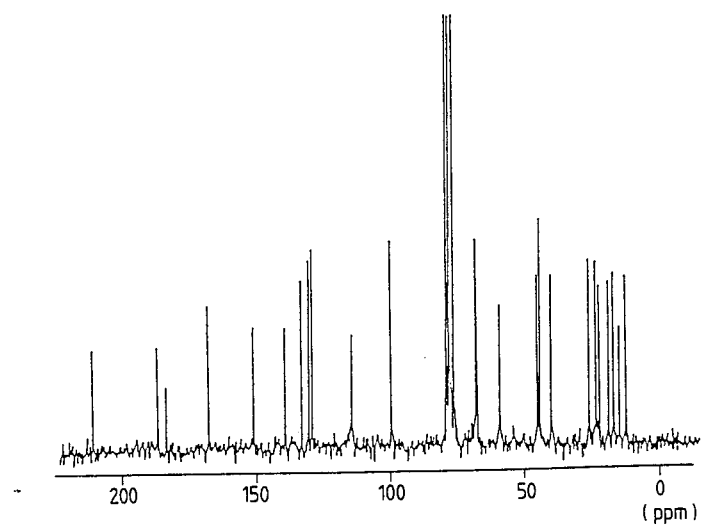
FIG. 8 shows a $^{13}$C-nuclear magnetic resonance spectrum of Q-1047-B substance.
Figure 9:
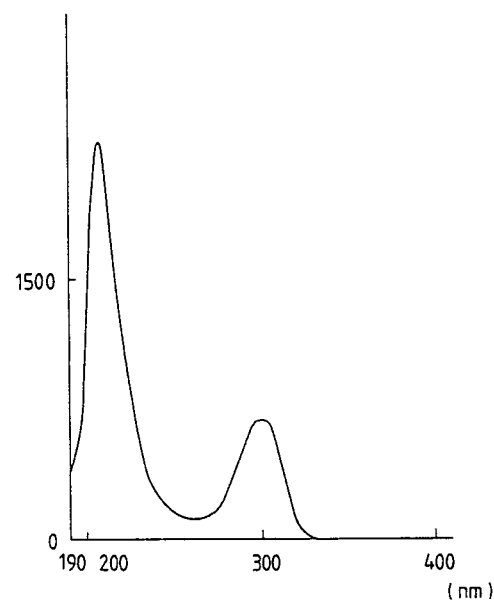
FIG. 9 shows an ultraviolet absorption spectrum of Q-1047R-A substance.
Figure 10:
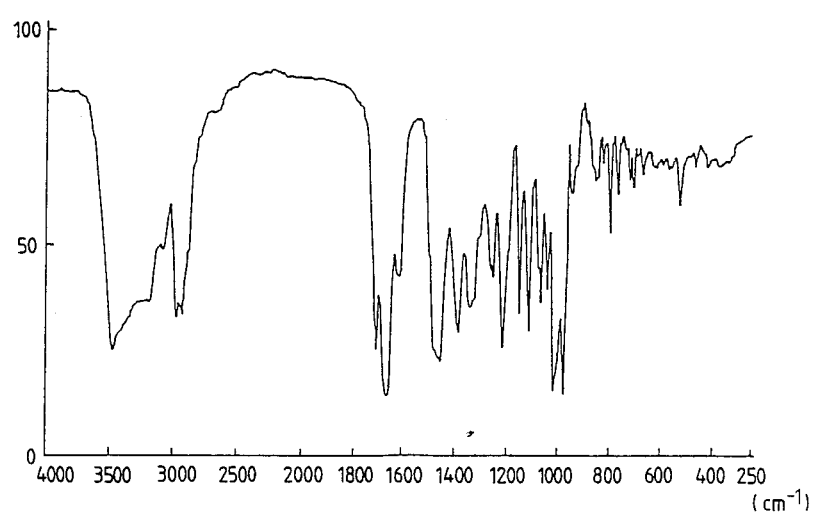
FIG. 10 shows an infrared absorption spectrum of Q-1047R-A substance.
Figure 11:
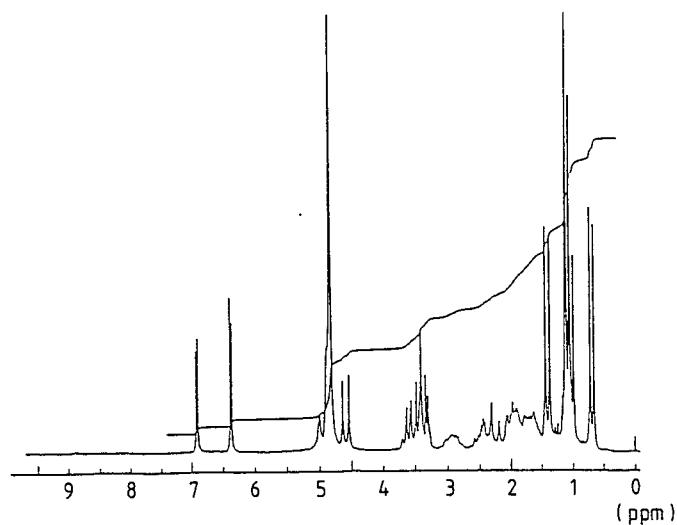
FIG. 11 shows a $^1$H-nuclear magnetic resonance spectrum of Q-1047R-A substance.
Figure 12:
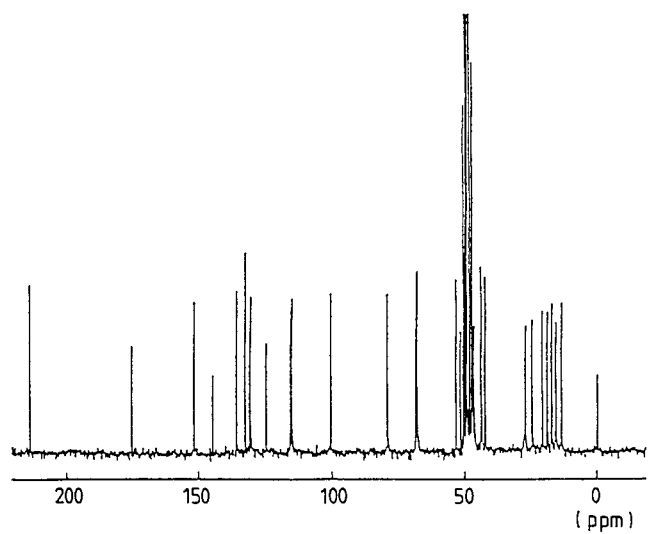
FIG. 12 shows a $^{13}$C-nuclear magnetic resonance spectrum of Q-1047R-A substance.
Figure 13:
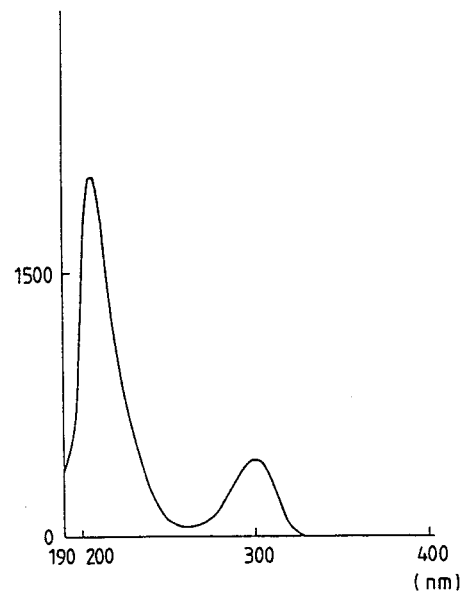
FIG. 13 shows an ultraviolet absorption spectrum of Q-1047R-B substance.
Figure 14:
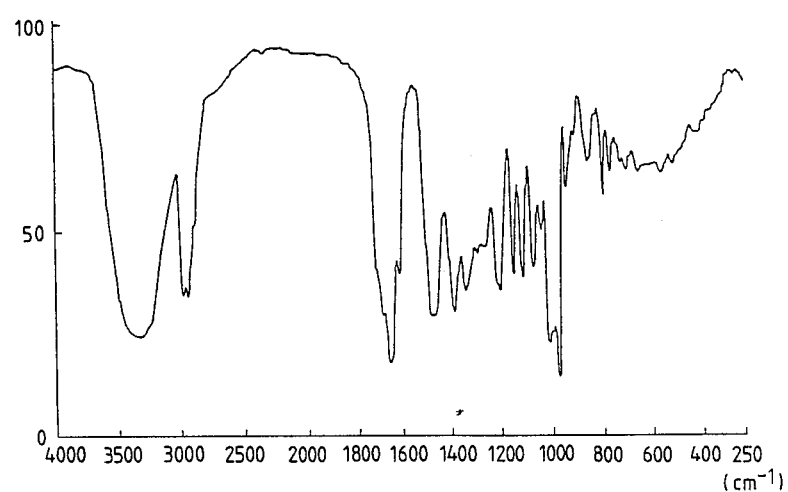
FIG. 14 shows an infrared absorption spectrum of Q-1047R-B substance.
Figure 15:
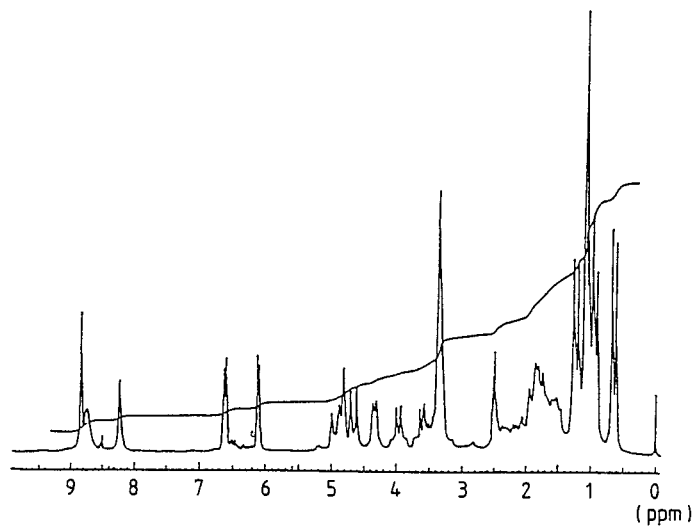
FIG. 15 shows a $^1$H-nuclear magnetic resonance spectrum of Q-1047R-B substance.
Figure 16:
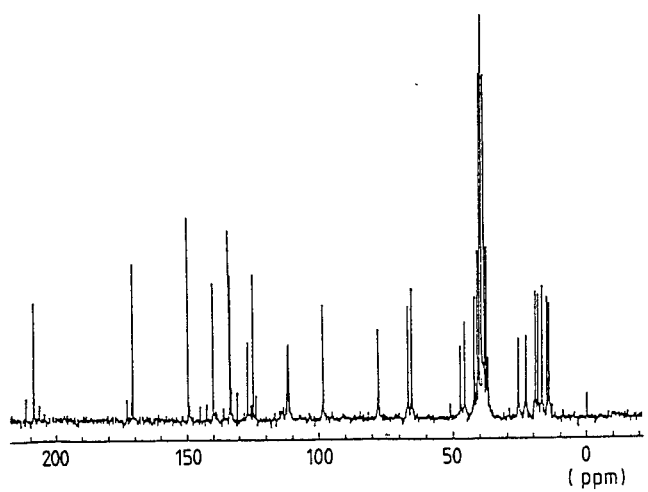
FIG. 16 shows a $^{13}$C-nuclear magnetic resonance spectrum of Q-1047R-B substance.

|  | Q-1047-A substance | Q-1047-B substance | Q-1047R-A substance | Q-1047R-B substance |
|---|---|---|---|---|
| (1) Ultraviolet absorption spectrum | FIG. 1 (in methanol) | FIG. 5 (in ethanol) | FIG. 9 (in methanol) | FIG. 13 (in methanol) |
| (2) Infrared absorption spectrum | FIG. 2 (KBr disk) | FIG. 6 (KBr disk) | FIG. 10 (KBr disk) | FIG. 14 (KBr disk) |
| (3) $^1$H-nuclear magnetic resonance spectrum | FIG. 3 (in CDCL$_3$, 500 MHz) | FIG. 7 (in CDCL$_3$, 100 MHz) | FIG. 11 (in DH$_3$—OH 100 MHz) | FIG. 15 (in DMSO-d$_6$, 100 MHz) |
| (4) $^{13}$C-nuclear magnetic resonance spectrum | FIG. 4 (in CDCL$_3$, 125 MHz) | FIG. 8 (in CDCL$_3$, 25 MHz) | FIG. 12 (in DH$_3$OH, 25 MHz) | FIG. 16 (in DMSO-d$_6$, 25 MHz) |
| (5) Mass analysis (FAB-MS) | 460 (MH+) | 460 (MH+) | 462 (MH+) | 462 (MH+) |
| (6) Molecular weight | 459 | 459 | 461 | 461 |
| (7) Molecular formula | C$_{25}$H$_{33}$NO$_7$ | C$_{25}$H$_{33}$NO$_7$ | C$_{25}$H$_{35}$NO$_7$ | C$_{25}$H$_{35}$NO$_7$ |
| (8) Appearance | Yellow platelets | Yellow platelets | Colorless powder | Colorless powder |
| (9) Melting point | 189–193° C. | 209–213° C. | 159–162° C. | 154–157° C. |
| (10) Specific rotation $[\alpha]_D^{25}$ | −43° (C = 1.0, CHCl$_3$) | −20° (C = 0.5, CHCl$_3$) | +25° (C = 1, methanol) | −17° (C = 1, methanol) |
| (11) Basic, neutral or acidic | Neutral substance | Neutral substance | Neutral substance | Neutral substance |
| (12) Solubility | Soluble in dioxane, chloroform, ethyl acetate, acetonitrile; sparingly soluble in toluene, benzene, ethanol, | Soluble in dioxane, chloroform, ethyl acetate, acetonitrile; sparingly soluble in toluene, | Soluble in ethyl acetate, acetonitrile, acetone, ethanol, methanol; sparingly soluble in dioxano, tolueno, | Soluble in ethyl acetate, acetonitrile, acetone, ethanol, methanol; sparingly soluble in dioxane, tolueno, |

TABLE 1-1-continued

| | Q-1047-A substance | Q-1047-B substance | Q-1047R-A substance | Q-1047R-B substance |
|---|---|---|---|---|
| | methanol; insoluble in water, hexane. | benzene, ethanol, methanol; insoluble in water, hexane. | benzene, chloroform; insoluble in water, hexane. | benzene, chloroform; insoluble in water, hexane. |
| (13) Thin layer chromatography [silica gel 60 $F_{254}$; detection under UV lamp (254 nm)] | Rf = 0.72 (chloroform-methanol = 9:1); Rf = 0.47 (benzene-acetone = 2:1); Rf = 0.67 (ethyl acetate-methanol = 15:1) | Rf = 0.67 (chloroform-methanol = 9:1); Rf = 0.43 (benzene-acetone = 2:1); Rf = 0.67 (ethyl acetate-methanol = 15:1) | Rf = 0.55 (chloroform-methanol = 5:1); Rf = 0.20 (benzene-acetone = 1:1); Rf = 0.44 (ethyl acetate-methanol = 10:1) | Rf = 0.46 (chloroform-methanol = 5:1); Rf = 0.14 (benzene-acetone = 1:1); Rf = 0.38 (ethyl acetate-methanol = 10:1) |

TABLE 1-2

Figure 17:
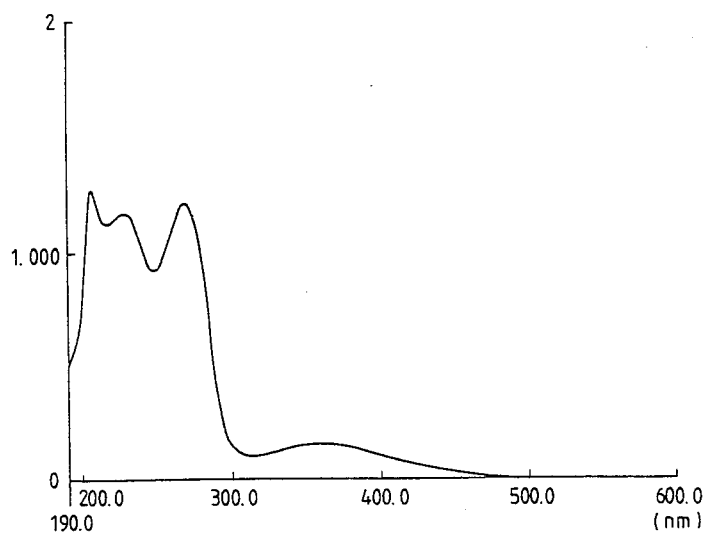
FIG. 17 shows an ultraviolet absorption spectrum of Q-1047H-A-A substance.
Figure 18:
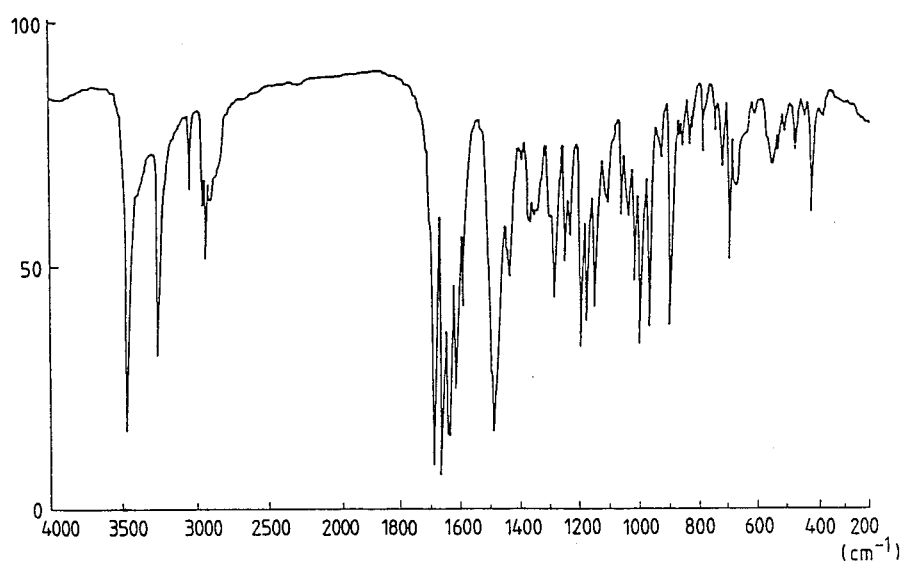
FIG. 18 shows an infrared absorption spectrum of Q-1047H-A-A substance.
Figure 19:
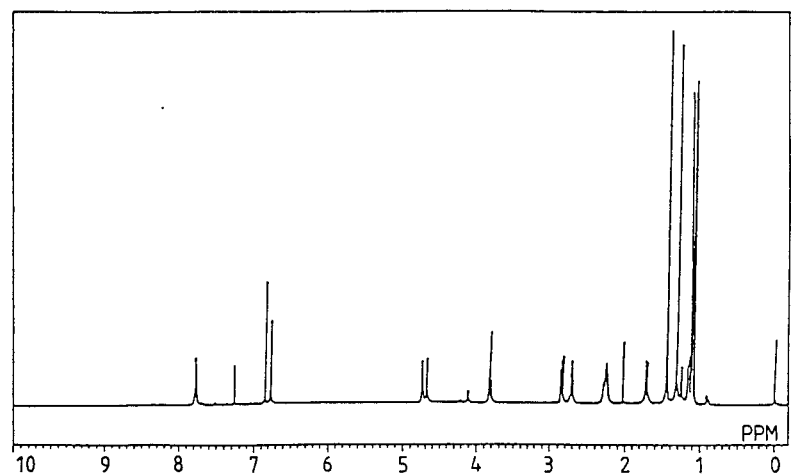
FIG. 19 shows a $^1$H-nuclear magnetic resonance spectrum of Q-1047H-A-A substance.
Figure 20:
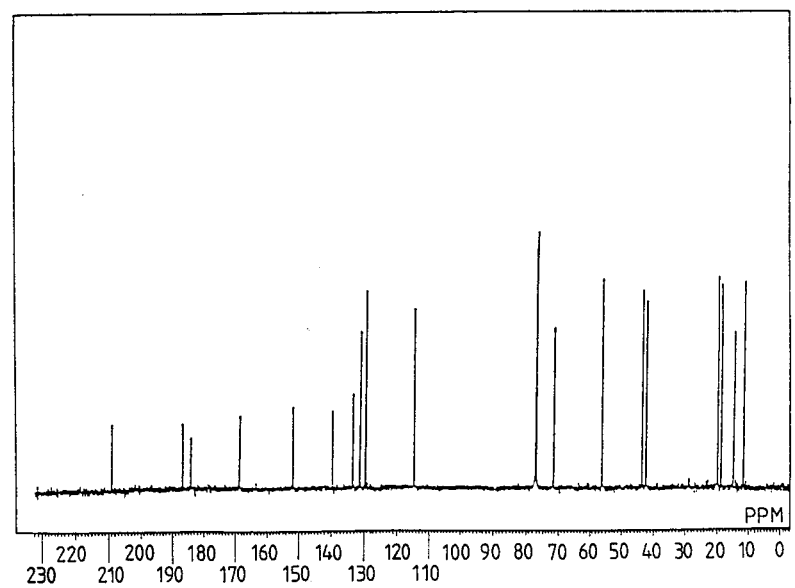
FIG. 20 shows a $^{13}$C-nuclear magnetic resonance spectrum of Q-1047H-A-A substance.
Figure 21:
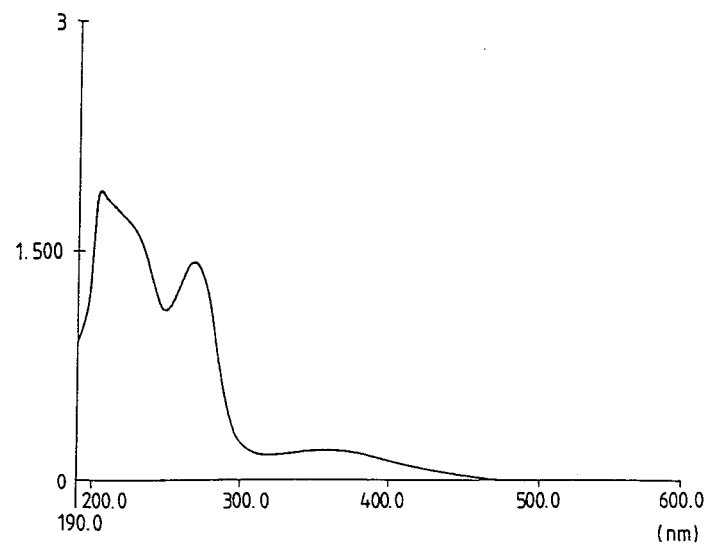
FIG. 21 shows an ultraviolet absorption spectrum of Q-1047H-A-B substance.
Figure 22:
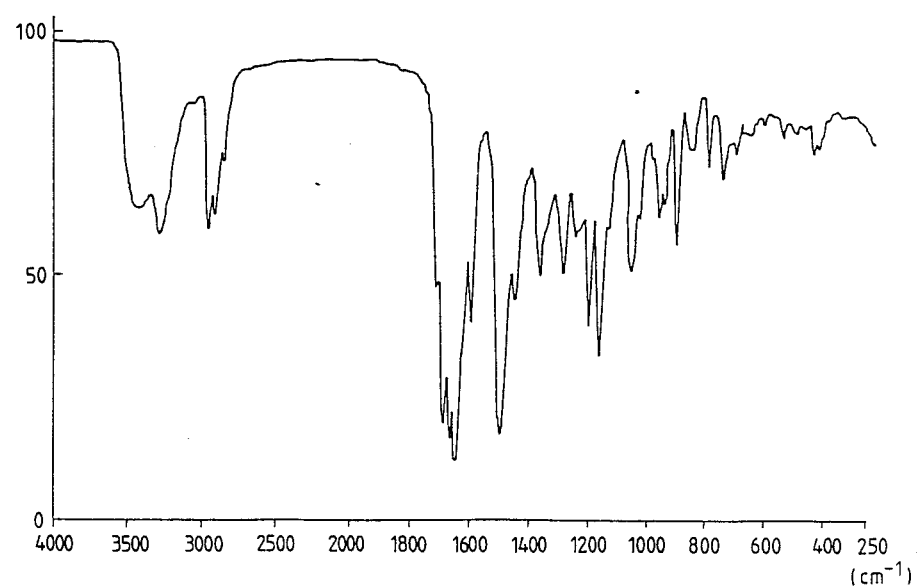
FIG. 22 shows an infrared absorption spectrum of Q-1047H-A-B substance.
Figure 23:
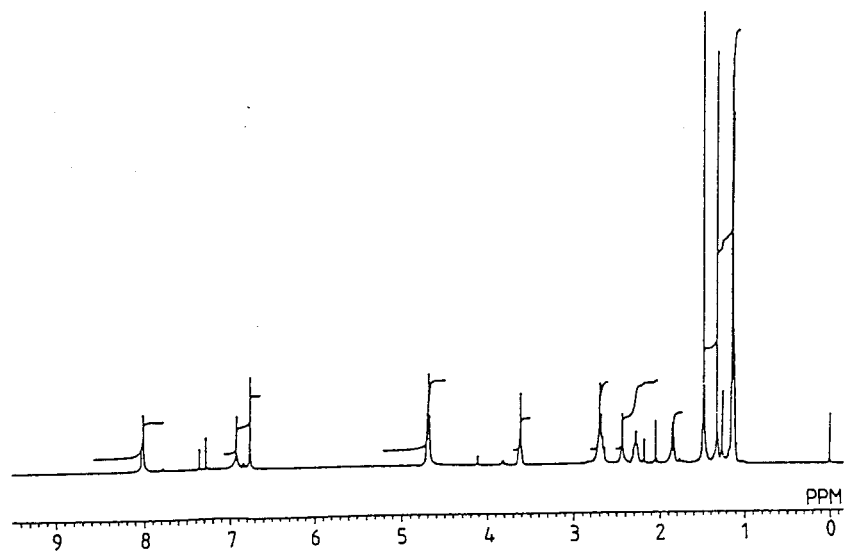
FIG. 23 shows a $^1$H-nuclear magnetic resonance spectrum of Q-1047H-A-B substance.
Figure 24:
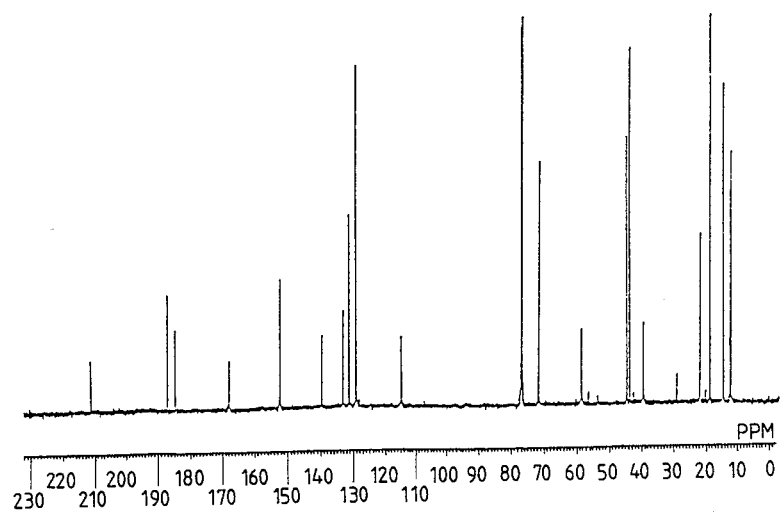
FIG. 24 shows a $^{13}$C-nuclear magnetic resonance spectrum of Q-1047H-A-B substance.
Figure 25:
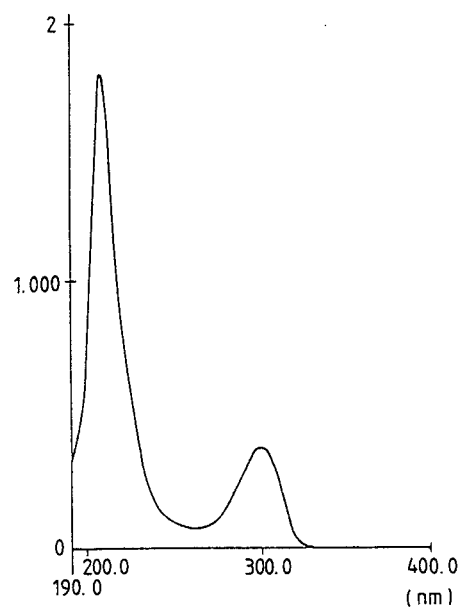
FIG. 25 shows an ultraviolet absorption spectrum of Q-1047H-R-A substance.
Figure 26:
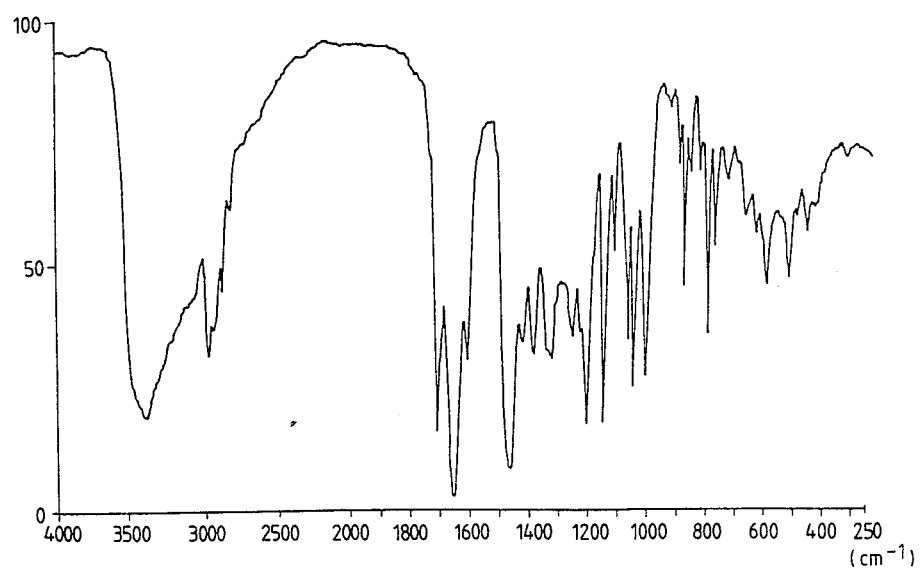
FIG. 26 shows an infrared absorption spectrum of Q-1047H-R-A substance.
Figure 27:
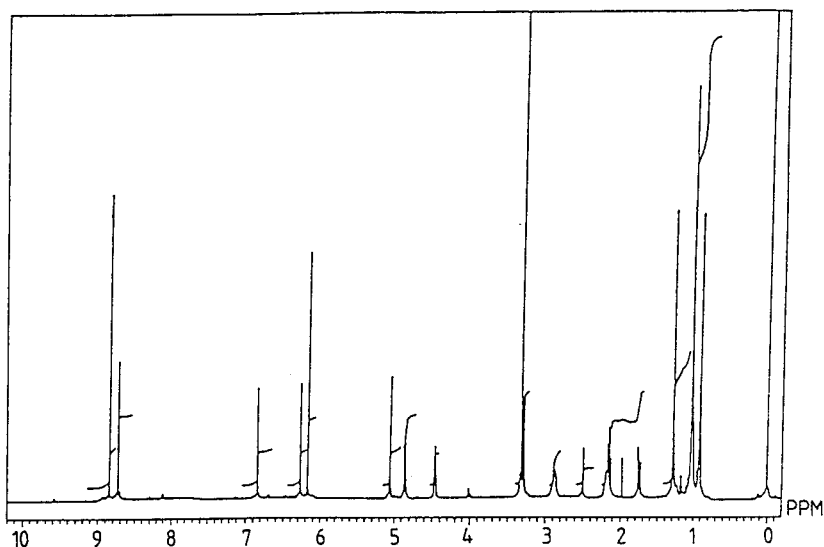
FIG. 27 shows a $^1$H-nuclear magnetic resonance spectrum of Q-1047H-R-A substance.
Figure 28:
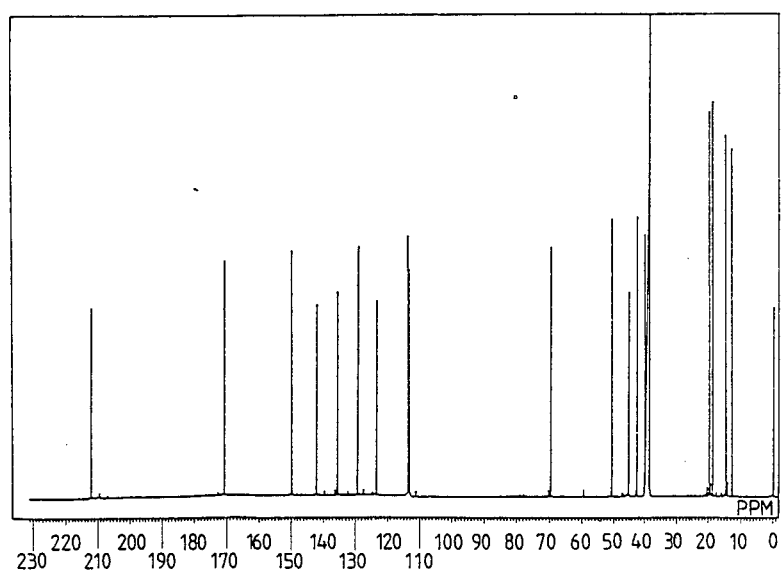
FIG. 28 shows a $^{13}$C-nuclear magnetic resonance spectrum of Q-1047H-R-A substance.

| | Q-1047H-A-A substance | Q-1047H-A-B substance | Q-1047H-R-A substance |
|---|---|---|---|
| (1) Ultraviolet absorption spectrum | FIG. 17 (in methanol) | FIG. 21 (in methanol) | FIG. 25 (in methanol) |
| (2) Infrared absorption spectrum | FIG. 18 (KBr disk) | FIG. 22 (KBr disk) | FIG. 26 (KBr disk) |
| (3) $^1$H-nuclear magnetic resonance spectrum | FIG. 19 (in CDCL$_3$, 500 MHz) | FIG. 23 (in CDCL$_3$, 500 MHz) | FIG. 27 (in DMSO-d$_6$, 500 MHz) |
| (4) $^{13}$C-nuclear magnetic resonance | FIG. 20 (in CDCL$_3$, 125 MHz) | FIG. 24 (in CDCL$_3$, 125 MHz) | FIG. 28 (in DMSO-d$_6$, 125 MHz) |
| (5) Mass analysis (FAB-MS) | 346 (MH$^+$) | 346 (MH$^+$) | 348 (MH$^+$) |
| (6) Molecular weight | 345 | 345 | 347 |
| (7) Molecular formula | $C_{19}H_{23}NO_5$ | $C_{19}H_{23}NO_5$ | $C_{19}H_{25}NO_5$ |
| (8) Appearance | Yellow platelets | Yellow platelets | Colorless platelets |
| (9) Melting point | 176–178° C. (decompt.) | 163–166° C. | 237–242° C. |
| (10) Specific rotation $[\alpha]_D^{25}$ | −68° (C = 1, CHCl$_3$) | −40° (C = 1, CHCl$_3$) | −7° (C = 1, methanol) |
| (11) Basic, neutral or acidic | Neutral substance | Neutral substance | Neutral substance |
| (12) Solubility | Soluble in dioxane, chloroform, ethyl acetate, acetonitrile; sparingly soluble in toluene, benzene, ethanol, methanol; insoluble in water hexane. | Soluble in dioxane, chloroform, ethyl acetate, acetonitrile; sparingly soluble in toluene, benzene, ethanol, methanol; insoluble in water hexane. | Soluble in ethyl acetate, acetonitrile, acetone, ethanol, methanol; sparingly soluble in dioxane, tolueno, benzene, chloroform; insoluble in water, hexane. |
| (13) Thin layer chromatography [silica gel 60 $F_{254}$; detection under UV lamp (254 nm)] | Rf = 0.55 (benzene-acetone = 3:1); Rf = 0.73 (chloroform-methanol = 9:1); Rf = 0.38 (benzene-ethyl acetate = 3:1) | Rf = 0.49 (benzene-acetone = 3:1); Rf = 0.69 (chloroform-methanol = 9:1); Rf = 0.28 (benzene-ethyl acetate = 3:1) | Rf = 0.3 (benzene-acetone = 1:1); Rf = 0.55 (chloroform-methanol = 5:1); Rf = 0.36 (benzene ethyl acetate-acetone = 1:2:2) |

The compounds according to the invention are usable, for example, as antiarrhythmics, drugs for myocardiac infarction, drugs for cerebral infarction, prophylactics for dementia and for senile dementia, circulation improving agents to be administered following subaraohnoid hemorrhage, for instance, renal function improving agents, therapeutic agents for stress peptic ulcers, antiarteriosclerotics, antiinflammatories, platelet aggregation inhibitors, therapeutic agents for autoimmune diseases, antirheumatics, antisclerodermatous agents; drugs for pulmonary fibrosis, antiretinopathic agents, and prophyloactic and therapeutic agents for cataract.

The compound according to the invention, which have a characteristic skeleton, are also highly useful as starting materials for the synthesis of useful derivatives.

The active oxygen species scavenging activities of the Q-1047 substances according to the invention are shown below together with the methods of measurement.

(A) Superoxide anion scavenging activity

Test method:

The compounds according to the invention were tested for superoxide anion scavenging activity by the method of McCord and Fridovich [J. Biol. Chem., 244 (22), 6049-6055 1969) . Thus, xanthine oxidase was added to $5 \times 10^{-2}$ M potassium phosphate buffer (pH 7.8) containing $1 \times 10^{-4}$ M EDTA, $1 \times 10^{-5}$ M ferricytochrome C and $5 \times 10^{-5}$ M xanthine to give a reaction system in which the rate of increase in absorbance at 550 nm as determined at 25° C. amounted to 0.025 per minute. One unit (u) of superoxide dismutase (SOD) activity was defined as the activity just sufficient to reduce the increase in absorbance at 550 nm in said reaction system by 50% and the superoxide anion scavenging activity of each compound tested was expressed in terms of that concentration of the compound which showed one unit of SOD activity.

Figure 29:
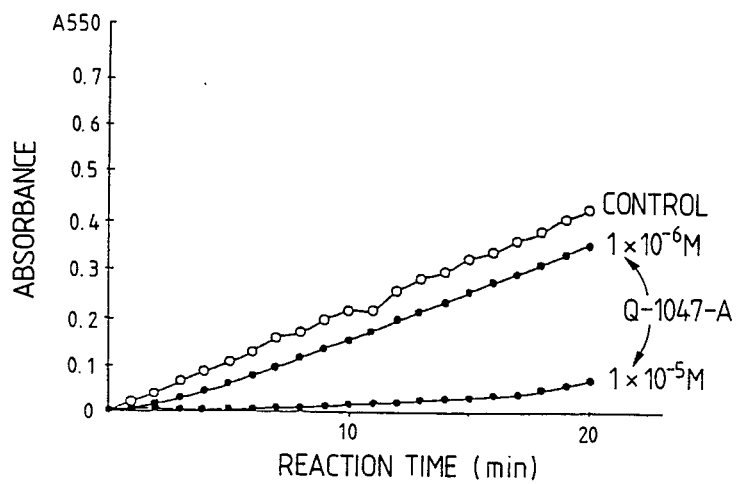
FIG. 29 shows the superoxide anion scavenging activity of Q-1047-A substance.
Figure 30:
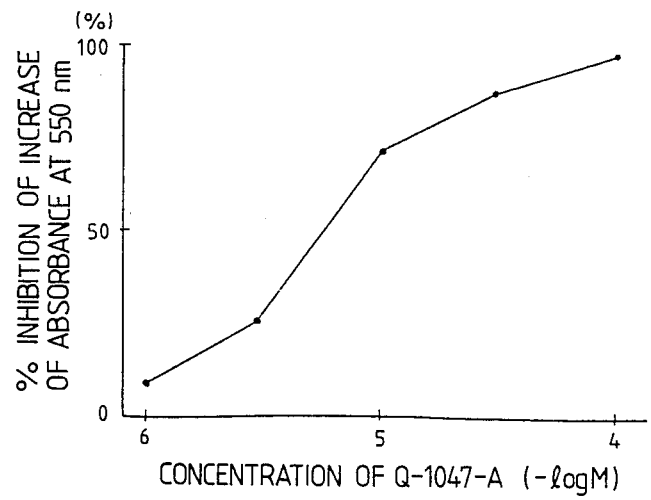
FIG. 30 shows that the superoxide anion scavenging activity of Q-1047-A substance is dependent on the concentration thereof.
Figure 31:
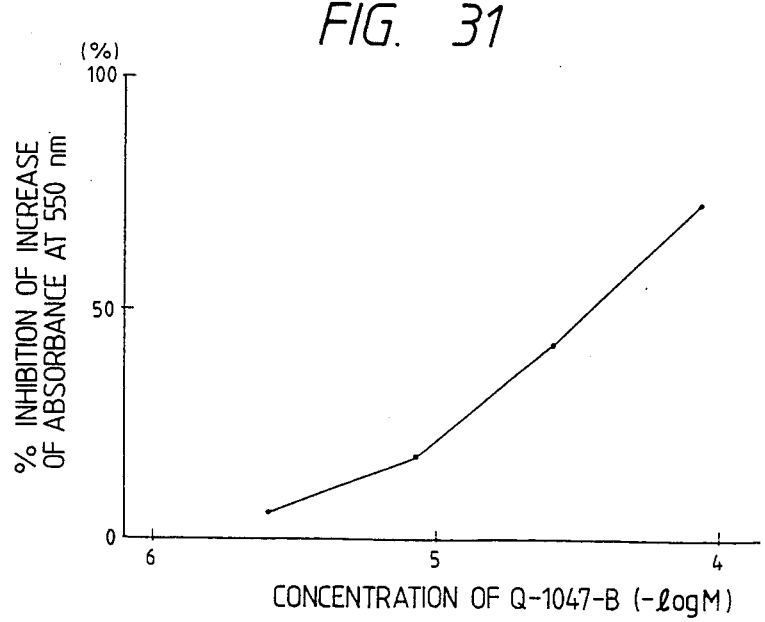
FIG. 31 shows that the superoxide anion scavenging activity of Q-1047-B substance is dependent on the concentration thereof.

Results:

The superoxide anion scavenging activity of Q-1047-A substance in the above reaction system is shown in FIG. 29, the concentration dependency of said activity is shown in FIG. 30, and the concentration dependency of the superoxide anion scavenging activity of Q-1047-B substance is shown in FIG. 31.

Figure 32:
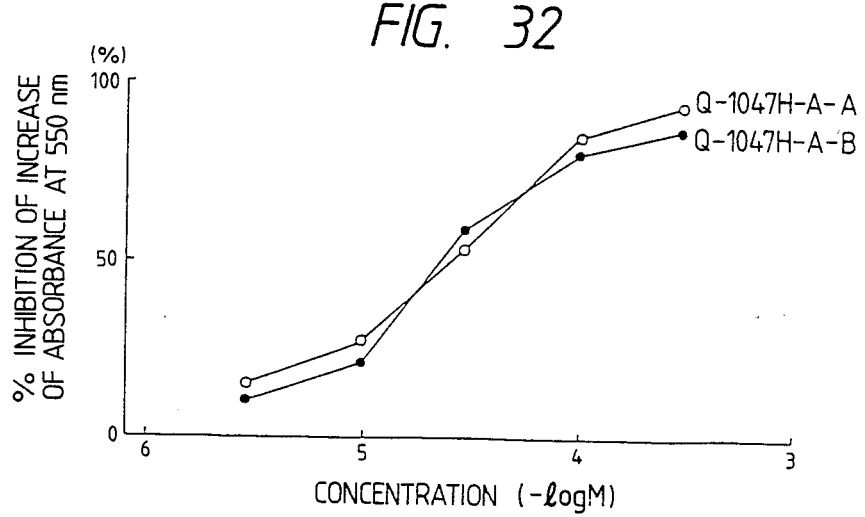
FIG. 32 shows that the superoxide anion scavenging activity of Q-1047H-A-A substance and of Q-1047H-A-B substance.

The concentration-dependent superoxide anion scavenging activities of Q-1047H-A-A substance and Q-1047H-A-B substance in the above reaction system are shown in FIG. 32.

In said reaction system, Q-1047-A substance showed one unit of SOD activity at the concentration of $5.6 \times 10^{-6}$ M and Q-1047-B substance at the concentration of $3.5 \times 10^{-5}$ M.

Q-1047H-A-A and Q-1047H-A-B substance have superoxide anion scavenging activity in said reaction system and showed one unit of SOD activity at the concentrations of $2.5 \times 10^{-5}$ M and $2.2 \times 10^{-5}$ M, respectively.

(B) Antioxidant activity

Test Method:

Generally, substances called antioxidants can decolorize 1,1-diphenyl-2-picrylhydrazyl (DPPH), which is a stable radical. Accordingly, the compounds according to the invention were tested for antioxidant activity in the following manner.

Thus, DPPH was dissolved in ethanol to a concentration of 0.1 mM, the test compound was admixed with the solution and, 30 minutes later, the absorbance was determined at 517 nm.

Figure 33:
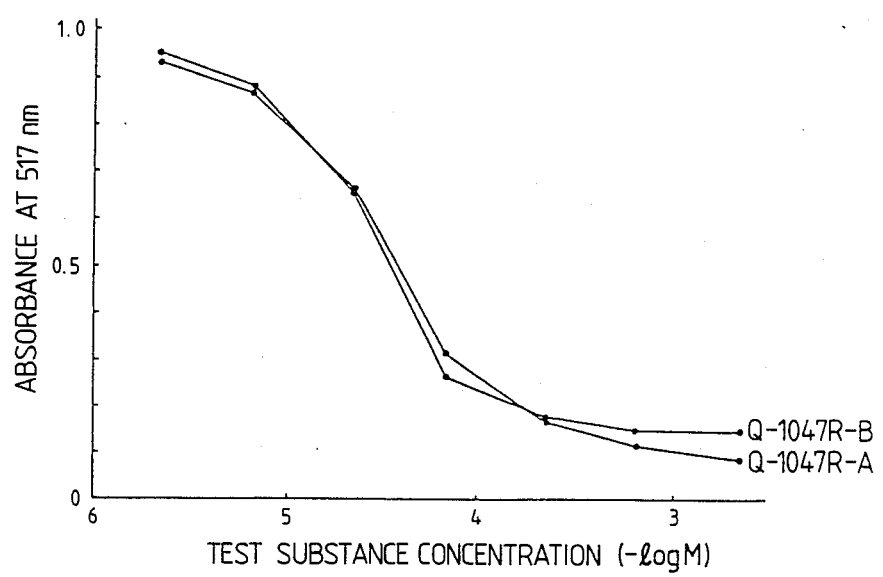
FIG. 33 shows that the antioxidant activity of Q-1047R-A substance and of Q-1047R-B substance.
Figure 34:
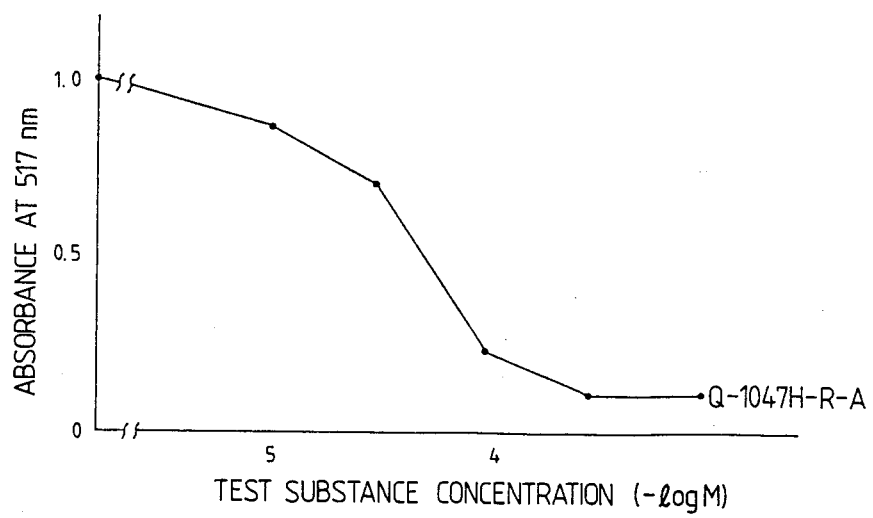
FIG. 34 shows the antioxidant activity of Q-1047H-R-A substance.

Results:

The results are shown in FIG. 33 and FIG. 34.

Q-1047R-A, Q-1047R-B and Q-1047H-R-A substances reduced the absorbance due to DPPH as measured at 517 nm.

These compounds presumably react with DPPH radical approximately in a mole ratio of 1:1 to show antioxidant activity.

(C) Effect on puromycin nephritis

Test method:

Male Sprague-Dawley rats (weighing 180-200 g) were used. Puromycin aminonucleoside (PAN) nephrosis rats were prepared by single intraperitoneal administration of 50 mg/kg of PAN. Throughout the experiment, the rats were fed in metabolic cages and received a solid diet for rats and tap water ad libitum. Urine samples were collected at timed intervals for 24 hours and assayed for protein content. The test drug, suspended in a 0.5% methylcellulose solution, was intraperitoneally administered daily. After the administration period, kidneys were excised, and thin sections were prepared therefrom in the conventional manner and examined microscopically.

Figure 35:
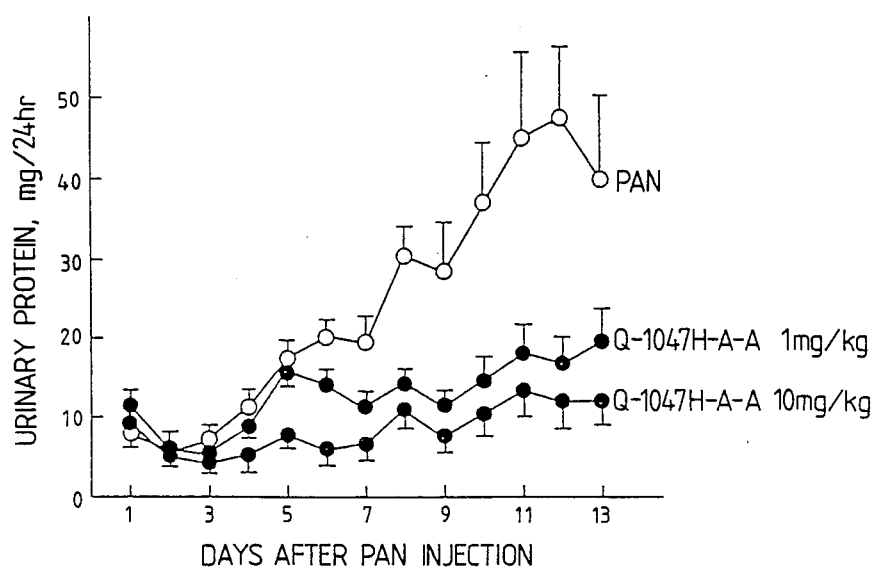
FIG. 35 shows the effect of Q-1047H-A-A substance on puromycin nephritis.

Results:

The results obtained are shown in FIG. 35.

In the group given PAN alone, the urinary protein level increased on the 7th day after administration of PAN. On the contrary, in the Q-1047H-A-A 10 mg/kg group, almost no increase in urinary protein was observed. In kidney tissue examination, the group given PAN alone showed degeneration and necrosis of glomerular capillary vessels, hypertrophy of endothelial cells, mesangial thickening due to hyperplasia of mesangial cells and deposition of hyaline droplet-like substance, whereas, in the group given 10 mg/kg of Q-1047H-A-A, such changes or abnormalities were lesser in extent and lower in incidence.

The compounds (I) according to the invention can be administered in a per se known manner either orally or non-orally in the form of pharmaceutical compositions (e.g. tablets, capsules (inclusive of soft capsules and microcapsules), solutions, suppositories, injections, nesal preparations) prepared by admixing with pharmacologically acceptable known carrier, excipients or diluents. The dose may vary depending on the target of administration, route of administration, symptom and other factors. Generally, however, in oral administration to mammals, the compounds (I) are used in a dose of about 0.1–100 mg/kg body weight, preferably about 0.5–50 mg/kg for example once to three times daily.

It is to be noted that the acute toxicity of Q-1047R-A substance in mice (LD$_{50}$, i.p.) is more than 500 mg/kg.

For non-oral administration, for example suppositories, the compounds (I) may be used in a dose of about 5–10 mg/kg once to twice daily. In the form of injections, the compounds (I) are desirably used in a dose of about 0.1–10 mg/kg once to twice daily.

In preparing the above-mentioned oral preparations, for example tablets, binders (e.g. hydroxypropylcellulose, hydroxymethylpropylmethylcellulose, Macrogol, etc.), disintegrants (e.g. starch, carboxymethylcellulose calcium, etc.), excipients (e.g. lactose, starch, etc.), lubricants (e.g. magnesium stearats, talc, etc. and other ingredients may be used each in an appropriate amount.

In manufacturing non-oral preparations, for example injections, isotonizing agents (e.g. glucose, D-sorbitol, D-mannitol, sodium chloride, etc.), preservatives (e.g. benzyl alcohol chlorobutanol, methyl p-hydroxybenzoate, propyl p-hydroxybenzoate, etc.), buffers (e.g. phosphate buffer, sodium acetate buffer, etc.) and other ingredients may be used each in an appropriate amount.

Since the compounds according to the invention are sparingly soluble in water, solubilizing agents (e.g. polyvinylpyrrolidone, triacetin, propylene glycol, etc.) may be incorporated, as necessary.

In the following, the methods of producing the compounds (I) according to the invention are described.

Method 1

The Q-1047 substances of the general formula (I$_1$)

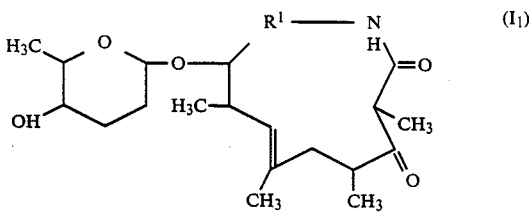

wherein R$^1$ is a group of the formula

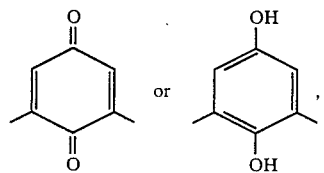

can be produced by cultivating a Q-1047 substance-producing microorganism belonging to the genus Pseudonocardia and directly recovering the substances from the culture.

As an example of the microorganism belonging to the genus Pseudonocardia and usable in the practice of the invention, there may be mentioned the strain Pseudonocardia sp. Q-1047 (FEMM P-9620, Internatonal Accession FERM No. BP-2331 under Budapest Treaty) isolated from a soil sample collected on an island of the Zamami Islands, Okinawa Prefecture, Japan. The bacteriological characteristics of the strain Q-1047 are described in the following.

(1) Morphology:

Said strain can grow on various synthetic and organic media. Its growth is good in particular on the sucrose nitrate agar, yeast malt agar, glycerin asparagine agar, tyrosine agar and the like media. The growth of serial hyphae is good on the sucrose nitrate agar, yeast malt agar, glycerin asparagine agar and tyrosine agar media, while aerial hyphae are invisible on the Bennett agar, peptone yeast iron agar and nutrient agar media. In observation under an light microscope, aerial hyphae grow on well-grown substrate hyphae, extending by acropetal germination and forming blastospores. Simultaneously, formation of arthrospores is observed.

Under an electron microscope, each spore chain consists of about 10 spores, with a spore size of 0.6–0.8 × 0.8–1.0 μm, the surface being smooth. No formation of whorls, sporangia or sclerotia is observable.

(2) Behaviors on various agar media

The behaviors on various agar media are as shown below in Table 2. Unless otherwise specified, cultivation was performed at 28° C. for 21 days and observation was made in the conventional manner. The colors were described in accordance with "guide to color standard" published by Nihon Shiki Sai Co., Ltd.

TABLE 2

| Medium | | | |
|---|---|---|---|
| Sucrose | G | Moderate | |
| nitrate | A | Grayish white | |
| agar | R | Colorless to grayish white | |
| | S | None | |
| Glucose | G | Poor | |
| asparagine | A | No growth | |
| agar | R | Colorless to brownish white | |
| | S | None | |
| Glycerin | G | Moderate | |
| asparagine | A | White to grayish white | |
| agar | R | Colorless | |
| (ISP-5) | S | None | |
| Starch | G | Poor | |
| inorganic | A | White (slight and thin growth) | |
| salt agar | R | Colorless | |
| (ISP-4) | S | None | |
| Tyrosine | G | Moderate | |
| agar | A | Grayish white | |
| (ISP-7) | R | Colorless to brownish white | |
| | S | None | |
| Nutrient | G | Poor | |
| agar | A | No growth | |
| | R | Brownish white | |
| | S | None | |

TABLE 2-continued

| Medium | | | |
|---|---|---|---|
| Yeast | G | Moderate | |
| malt | A | Brownish white | |
| agar | R | Pale yellow to pale yellowish brown | |
| (ISP-2) | S | Brown (around 5th day and thereafter) | |
| Oatmeal | G | Moderate | |
| agar | A | White to grayish white | |
| (ISP-3) | R | Pale yellow to pale yellowish brown | |
| | S | Yellow (around 5th day and thereafter) | |
| Bennett | G | Moderate | |
| agar | A | No growth | |
| | R | Pale yellow to pale yellowish brown | |
| | S | Yellow (around 5th day and thereafter) | |
| Peptone | G | Moderate | |
| yeast | A | No growth | |
| iron agar | R | Pale yellow to pale yellowish brown | |
| (ISP-6) | S | None | |
| Simmons | G | No growth | |
| agar | A | | |
| | R | | |
| | S | | |

Notes:
G: Growth and colony surface color
A: Growth and color of aerial hyphae
R: Reverse side color
S: Soluble pigments (3) Physiological properties

| Physiological properties | | |
|---|---|---|
| (1) Temperature range for growth | | 25–45° C. |
| Optimum temperature for growth | | 30–32° C. |
| (2) Gelatin liquefaction | | |
| Gelatin only (25° C.) | | Weakly positive |
| Glucose-peptone-gelatin (28° C.) | | Negative |
| (3) Milk coagulation | | Negative |
| Milk peptonization | | Negative |
| (4) Nitrate reduction | | Positive |
| (5) Starch hydrolysis | | Negative |
| (6) Melanoid pigment formation | | |
| Tryptone-yeast extract broth | | Negative |
| Tyrosine agar | | Negative |
| Paptone-yeast-iron agar | | Negative |
| (7) Growth on NaCl-containing media | | |
| Can grow at 3% NaCl but cannot grow at 5% NaCl or higher. | | |

Notes:
The temperature range for growth is based on the results observation after 7–21 days of incubation at 5,10,15,20,25,28,30,33,37,40,45 and 50° C.
The actions on milk are based on the results of observation after 3–21 days of incubation at 37° C. Unless otherwise specified, other properties are based on the results of observation after 2 weeks of incubation at 28° C.

(4) Carbon source utilization (Pridham-Gottilieb agar medium, incubation at 28° C.):

| | |
|---|---|
| L-Arabinose | − |
| D-Xylose | + |
| D-Glucose | + |
| D-Fructose | − |
| Sucrose | +− |
| Inositol | − |
| Rhamnose | + |
| Raffinose | − |
| D-Mannitol | + |
| Trehalose | + |
| D-Galactose | +− |
| Mannose | − |
| Lactose | − |
| α-Melibiose | − |
| Salicin | + |
| Glycerin | + |

-continued

| | |
|---|---|
| Starch | + |

Notes:
+: growth;
+−: suspected growth;
−: no growth (5) Chemotaxonomy:

The above strain was chemically classified by the method of Lechvalier et al. (Lechvalier, M.P. et al.: pp.277–238 in Diets, A. et al. (ed.): Actinomycete Taxonomy, SIM Special Publication No. 6, 1980) as follows:

| | |
|---|---|
| Cell wall type | IV (meso-diaminopimelic acid, arabinose and galactose) |
| Sugar pattern of whole cell extract | A (arabinose and galactose) |
| Phospholipids | Type III |
| Micolic acids | Not detected |

To sum up, the strain Q 1047 extends aerial hyphae by acropetal germination, forming blastospores and at the same time arthrospores. Spores are observed also on substrate hyphae. The spore surface is smooth, and no whorls or sporangia are observable. According to the results of chemical analysis of the cell and cell wall, the strain belongs to the cell wall type IV-A.

On the basis of the above properties, known bacterial strains similar to the above-mentioned strain Q-1047 were sought for referring to Bergey's Manual of Determinative Bacteriology, 8th edition, 1974; International Journal of Systematic Bacteriology, 18(2), 69–189 (1968), ibid., 18 (4), 279–392 (1968), ibid., 19 (4), 391–512 (1969), ibid., 22 (4), 265–394 (1972); and other references. As a result, the genera Actinopolyspora, Saccharopolyspora, Pseudonocardia and Faenia were found to possibly include the strain Q-1047. However, Actinopolyspora species are salt-resistant. Saccharopolyspora species are quite different in spore surface structure from the strain Q-1047; they are different from the strain Q-1047 also in that they form spores only at the top of the aerial hypha. Faenia species do not form aerial hyphae acropetally; they can grown on many media at 35°–60° C. while the strain Q-1047 can grow only in the temperature range of 24°–25° C.. On the other hand, Pseudonocardia species, which form spores on aerial hyphae and on substrate hyphae and form long cylinder-like spores acropetally, have many properties in common to the strain Q-1047. Therefore, said strain was judged to be most reasonably classifiable as a strain belonging to the genus Pseudonocardia and, for the time being, named Pseudonocardia sp. Q-1047.

Said strain has been deposited at the Fermentation Research Institute, Agency of Industrial Science and Technology, Ministry of International Trade and Industry, Japan, under the deposit number FERM P-9620 (confromity with the International Accession Number FERM BP-2331 under Budapest Treaty). Microorganisms in general are susceptible to artificial and spontaneous mutations. Thus, the Pseudonocardia sp. Q-1047 includes not only a corresponding actinomycete isolated from a natural source but also spontaneous mutants thereof and mutants derived therefrom artificially by means of ultraviolet rays, X-rays, chemical agents and so forth.

Q-1047 substances can be produced fermentatively in the following manner.

The Pseudonocardia sp. Q-1047 is cultivated in a medium and Q-1047 substances produced are recovered from the culture. The cultivation is carried out in the conventional manner of cultivation of microorganisms in general. Generally, however, the cultivation is advantageously carried out in the manner of submerged culture in a liquid medium. Any medium which contains nutrients utilizable by the Pseudonocardia sp. Q-1047 may be used as the medium.

Thus, synthetic media, semisynthetic media or natural media are usable. The media may contain such carbon sources as glucose, arabinose, fructose, starch, vegetable oils, etc. and such nitrogen sources as meat extract, peptone, gluten meal, cottonseed cake, soya flour, peanut flour, fish meal, corn steep liquor, dried yeast, yeast extract, ammonium sulfate, ammonium nitrate, urea and/or other organic or inorganic nitrogen sources. If necessary, sulfates, nitrates, chlorides, carbonates, phosphates and other salts of Na, K, Mg, Ca, Zn, Fe and so forth may be added as metal salts.

Furthermore, substances capable of promoting formation of antibiotics or antifoam agents; such a methionine, cysteine, systine, thiosulfates, methyl oleate, lard oil, silicones, surfactants, etc., may also be added as necessary.

Generally the cultivation is advantageously carried out under aerobic conditions. The cultivation temperature is desirably within the range of about 25°–45° C., preferably about 28° C.. Good results are obtained when the pH of the medium is maintained in the range of about 5–10, preferably about 6–8. The cultivation period is suitably selected depending on the medium composition and temperature conditions.

The desired Q-1047 substances can be recovered or isolated from the culture by any of the conventional methods know for the isolation of antibiotics from cultures of microorganisms. Since the desired products are contained in the culture fluid phase, cells are removed by filtration or centrifugation and active substances are extracted from the filtrate. Thus, the active substances are separated, recovered and purified by conventional means generally employed in the production of antibiotics which make good use of the solubility and difference in solubility in an appropriate solvent, precipitability from a solution and difference in rate of precipitation, difference in adsorptive affinity for an adsorbent, difference in distribution in two different liquid phases, and so forth. These means are use either singly or in combination in any appropriate order, as the case may be. Said means may also be applied repeatedly as necessary.

The desired substance Q-1047-A or Q-1047-B in which $R^1$ is a group of the formula

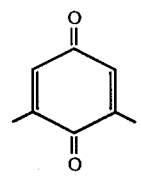

differs in polarity from Q-1047R-A or Q-1047R-B in which $R^1$ is a group of the formula

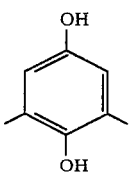

and therefore these substances can be separated from each other with ease by making use of the difference in polarity, namely by silica gel column chromatography, for instance.

Method 2

Among the compounds according to the invention, Q-1047H substances ($I_2$) can be produced by the method illustrated by the following reaction formula:

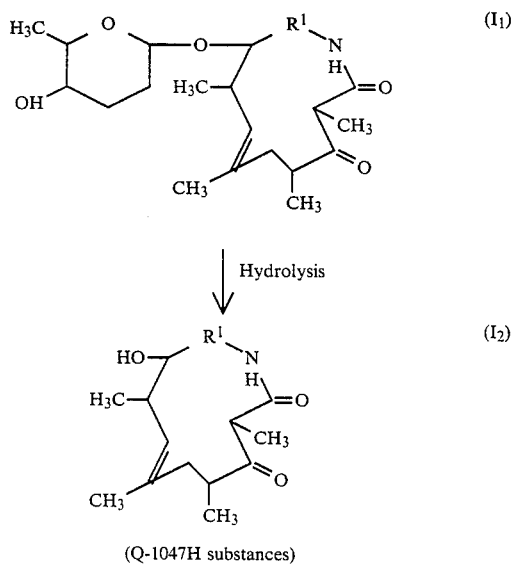

(Q-1047H substances)

In the above formula, $R^1$ is as defined above.

Thus, Q-1047H substances can be produced by hydrolyzing the compound or compounds of general formula ($I_1$) obtained by method 1.

The hydrolysis is generally effected with an acid. Usable as the acid catalyst for acid hydrolysis are inorganic acids such as hydrochloric acid, sulfuric acid, nitric acid, perchloric acid, periodic acid and perbromic acid, and organic acids, such as trifluoroacetic acid, methanesulfonic acid camphorsulfonic acid, p-toluenesulfonic acid, trichloroacetic acid, tribromoacetic acid, dichloroacetic acid and dibromoacetic acid. The reaction is carried out in the presence of an acid catalyst such as mentioned above in water or an alcohol or in a mixed solvent composed of water and an organic solvent, such as an alcohol, a carboxylic acid, acetonitrile, tetrahydrofuran or dioxane, with cooling or at room temperature or with warming, for instance.

Method 3

As an alternative method of producing the compounds according to the invention, there may be mentioned a method comprising conversion of one desired compound to another. Said method comprises reducing a compound of general formula (I) in which $R^1$ is in the benzoquinone form or oxidizing a compound of general formula (I) in which $R^1$ is in the hydroquinone form.

For the reduction, any conventional method of reduction which is generally applicable to the reduction of benzoquinones. Thus, for example, sodium hydrosulfite, sodium hydrogen sulfite, sodium brohydride or the like may be used. Any solvent inert to the reaction may be used as the reaction solvent. The reducing agent is used in an amount of 1-200 moles per mole of the starting compound. The reaction temperature is not critical. Generally, however, the reaction is carried out at 0°-40° C., preferably at room temperature. The necessary reaction time may very depending on the reducing agent and reaction temperature but, generally, the reaction comes to completion readily in about several tens of seconds to 24 hours.

For the oxidation, any method generally used for oxidizing hydroquinones may be used.

Thus, for instance, ferric chloride, ferric sulfate, potassium ferricyanide, silver oxide, oxygen (air) or the like may be used as the oxidizing agent. Any solvent inert to the reaction may be used as the solvent. The oxidizing agent is used in an amount of 1-200 moles per mole of the starting compound. Although the reaction temperature is not critical, the reaction is generally carried out at 0°-40° C., preferably at room temperature. The necessary reaction time may vary depending on the oxidizing agent and reaction temperature but, generally, the reaction comes to completion readily in about several tens of seconds to 24 hours.

In producing the compounds according to the invention by method 2 or 3, the compounds produced in the culture liquid phase may be subjected directly, without isolation thereof from said liquid phase, to hydrolysis and/or oxidation or reduction, as desired, to give a desired compound or compounds.

The present invention is now illustrated in greater detail by way of the following Examples, but it should be understood that the present invention is not deemed to be limited thereto. In these examples, all parts, ratios and percentages are by weight unless otherwise indicated.

Example 1

A medium (pH 7.3) containing 1.0% glucose, 0.1% yeast extract, 0.2% NZ amine type A and 0.1% meat extract was prepared, distributed in 60-ml portions into 500-ml Erlenmeyer flasks, sterilized at 120° C. for 20 minutes, and inoculated with mycelia scratched off from a culture of Pseudonocardia sp. Q-1047 grown on Bennetts agar medium. Shake culture at 28° C. for 48 hours gave a seed culture. Then, a medium (pH 7.3; 15 liters) containing 1.0% mannitol and 0.4% yeast extract was prepared, distributed in 60-ml portions into 500-ml Erlenmeyer flasks, sterilized at 120° C. for 20 minutes, and inoculated with the seed culture in an amount of 3.0% (v/v). Shake culture was continued at 28° C. for 120 hours.

Radiolite No. 600 (Showa Chemical Industry) was added to the culture thus obtained, and the mixture was stirred and then filtered to give a filtrate (13 liters). The filtrate was adjusted to pH 7.0, 13 liters of ethyl acetate was added thereto, and the mixture was stirred thoroughly. The ethyl acetate layer was separated and dehydrated on anhydrous sodium sulfate. The thus-dehydrated ethyl acetate layer was concentrated under reduced pressure to give 3.2 g of a brown powder. The brown power obtained (3.2 g) was dissolved in a small amount of chloroform, and the solution was subjected to column chromatography on a column packed with 100 g of Wakogel C-200 (Wako Pure Chemical Industries) by means of chloroform, using chloroform-methanol (100:1, v/v) as the developing solvent. Simple silica gel thin layer chromatography was used for the detection of Q-1047 substances. Thus, each eluate fraction from the column was spotted on a silica gel 60F$_{254}$ TLC plate (Merck) and developed with a chloroform-methanol (9:1, v/v) mixture. The plate was irradiated with an ultraviolet lamp (254 nm) for the detection of Q-1047-A substance showing an Rf value of 0.72 and having an SOD-like activity. Column chromatography fractions containing Q-1047-A substance alone were combined and concentrated under reduced pressure to give 1.7 g of pure Q-1047-A substance as a yellow microcrystalline powder. Crystallization of this yellow microcrystalline powder from a hexane-chloroform mixture (1:50, v/v) gave Q-1047-A substance as yellow plate crystals.

Similarly, Q-1047-B substance was detected which showed an Rf value of 0.67 and an SOD-like activity. Column chromatography fractions containing Q-1047-B substance alone were combined and concentrated under reduced pressure to give 70 mg of Q-1047-B substance as a yellow microcrystalline powder. Recrystallization of this yellow microcrystalline powder from a hexane-chloroform mixture (1:50, v/v) gave Q-1047-B substance as yellow plate crystals.

Example 2

A medium (pH 7.3) containing 1.0% glucose, 0.1% yeast extract, 0.2% NZ amine type A and 0.1% meat extract was prepared, distributed in 60-ml portions into 500-ml erlenmeyer flasks, sterilized at 120° C. for 20 minutes, and inoculated with mycelia scratched off from a culture of Pseudonocardia sp. Q-1047 grown on Bennetts agar medium and shake culture was conducted at 28° C. for 48 hours to give a seed culture. Then, a medium (pH 7.3; 10 liters) containing 3.0% mannitol and 1.0% yeast extract was prepared, distributed in 100-ml portions into 500-ml erlenmeyer flasks, sterilized at 120° C. for 20 minutes, and inoculated with the seed culture in an amount of 3%(v/v). Shake culture was continued at 28° C. for 96 hours.

Radiolite No. 600 (Showa Chemical Industry) was added to the thus-obtained culture, and the mixture was stirred and then filtered to give a filtrate (8 liters). The filtrate wa adjusted to pH 7.0, 10 liters of ethyl acetate was added thereto, and the mixture was stirred thoroughly. The ethyl acetate was separated and dried over anhydrous sodium sulfate. The thus-dried ethyl acetate layer was concentrated under reduced pressure to give 3 g of a brown powder. The brown powder obtained (3 g) was dissolved in a small amount of a chloroform-methanol (50:1, v/v) mixture, and the solution was applied to a column packed with 60 g of Wakogel C-200 (Wako Pure Chemical Industries) by means of a chloroform-methanol (50:1, v/v) mixture. Then, column chromatography was performed using chloroform-methanol (40:1, v/v) as the developing solvent. Simple silica gel thin layer chromatography was used for the detection of Q-1047R substance. Thus, each column chromatography eluate fraction was spotted on a silica gel 60F$_{254}$ TLC plate (Merck) and developed with a chloroform-methanol (5:1, v/v) mixture. The plate was irradiated with an ultraviolet lamp (254 m) and Q-1047R-A substance was detected which showed an Rf value of 0.55 and had an antioxidant activity. Column chromatography fractions containing Q-1047R-A substance alone were combined and concentrated under reduced pressure to give 2.1 g of pure Q-1047R-A substance as a colorless powder. Detection of Q-1047R-B substance having an Rf value of 0.46 and an antioxidant activity was performed in the same manner. Column chromatography fractions containing Q-1047R-B substance alone were combined and concentrated under reduced pressure to give 120 mg of pure Q-1047R-B substance as a colorless powder.

Example 3

(a) One gram of Q-1047-A substance was dissolved in 300 ml of ethyl acetate, 100 ml of 2% aqueous solution of sodium hydrosulfite was added to the solution, and the mixture was stirred thoroughly in a separating funnel for effecting reduction of Q-1047-A substance. The ethyl acetate layer was washed with two 100-ml portions of water, dehydrated over anhydrous sodium sulfate and then concentrated under reduced pressure to give 600 mg of pure Q-1047R-A substance as a colorless crystalline powder.

(b) To a solution of 500 mg of Q-1047-B substance in 200 ml of ethyl acetate was added 50 ml of 2% aqueous solution of sodium hydrosulfite. The mixture was stirred thoroughly in a separating funnel for causing reduction of Q-1047-B substance. The ethyl acetate layer was washed with two 50 ml portions of water, dehydrated on anhydrous sodium sulfate and concentrated under reduced pressure to give 300 mg of pure Q-1047R-B substance as a colorless crystalline powder.

Example 4

One gram of Q-1047-A substance was dissolved in a mixed solvent composed of 50 ml of acetonitrile and 50 ml of 0.5 N hydrochloric acid, and acid hydrolysis was effected at room temperature for 30 minutes. After reaction, the reaction mixture was concentrated under reduced pressure to remove the acetonitrile. To the concentrated reaction mixture (about 50 ml) was added 70 ml of ethyl acetate, and extraction was effected to a good extent. After two repetitions of this extraction procedure, the combined ethyl acetate layer was washed with 50 ml of 2% NaHCO$_3$ solution and then with two 50-ml portions of water, anhydrous sodium sulfate was added to the ethyl acetate layer thus obtained, and dehydration was effected thoroughly. The thus-dehydrated ethyl acetate layer was concentrated under reduced pressure to give 800 mg of a yellow microcrystalline powder. This powder (800 mg) was dissolved in a small amount of a benzene-acetone (10:1, v/v) mixture, the solution was applied to a column packed with 16 g of Wakogel C-200 (Wako Pure Chemical Industries) by means of benzene, and column chromatography was carried out using benzene-acetone (10:1, v/v) as the developing solvent. Simple silica gel thin layer chromatography was used for the detection of Q-1047H-A-A substance. Thus, each column chromatography eluate fraction was spotted on a silica gel 60F$_{254}$ TLC plate (Merck) and developed with a benzene-acetone (3:1, v/v) mixture. Q-1047H-A-A substance showing an Rf value of 0.55 and an SOD-like activity was detected under irradiation with an ultraviolet lamp (254 nm). Column chromatography fractions containing Q-1047H-A-A substance alone were combined and concentrated under reduced pressure to give 650 mg of pure Q-1047H-A-A substance as a yellow microcrystalline powder. Crystallization of this yellow microcrystalline powder from a benzene-acetone mixture (5:1, v/v) gave Q-1047H-A-A substance as yellow plate crystals.

Example 5

Q-1047-B substance (600 mg) was dissolved in a mixed solvent composed of 30 ml of acetonitrile and 30 ml of 0.5 N hydrochloric acid, and acid hydrolysis was effected at room temperature for 30 minutes. After reaction, the reaction mixture was concentrated under reduced pressure to remove the acetonitrile. To the concentrated reaction mixture (about 30 ml) was added 50 ml of ethyl acetate, and extraction was effected to a good extent. After two repetitions of this extraction procedure, the combined ethyl acetate layer was washed with 40 ml of 2% $NaHCO_3$ solution and further with two 40-ml portions of water, thoroughly dehydrated over anhydrous sodium sulfate, and concentrated under reduced pressure to give 480 mg of a yellow microcrystalline powder. The yellow powder (480 mg) was dissolved in a small amount of a benzene-acetone (10:1, v/v) mixture, the solution was put on a column packed with 10 g of Wakogel C-200 (Wako Pure Chemical Industries) by means of benzene, and column chromatography was carried out using benzene-acetone (10:1, v/v) as the developing solvent. Simple silica gel thin layer chromatography was used for the detection of Q-1047H-A-B substance. Thus, each column chromatography eluate fraction was spotted on a silica gel $60F_{254}$ TLC plate (Merck) and developed with a benzene-acetone (3:1, v/v) mixture. Q-1047H-A-B substance showing an Rf value of 0.49 and an SOD-like activity was detected under irradiation with an ultraviolet lamp (254 nm). Column chromatography fractions containing Q-1047H-A-B substance alone were combined and concentrated under reduced pressure to give 390 mg of pure Q-1047H-A-B substance as a yellow microcrystalline powder. Crystallization of this yellow powder from a mixed solvent (5:1, v/v) composed of benzene and acetone gave Q-1047H-A-B substance as yellow platelets.

Example 6

To a solution of 500 mg Q-1047H-A-A substance in 200 ml of ethyl acetate was added 70 ml of 2% sodium hydrosulfite solution. The mixture was stirred thoroughly in a separating funnel. This procedure was repeated twice for causing reduction of Q-1047H-A-A substance. The ethyl acetate layer obtained was washed with two 50-ml portions of water, thoroughly dehydrated over anhydrous sodium sulfate, and concentrated under reduced pressure to give 300 mg of Q-1047H-R-A substance as a colorless microcrystalline powder showing an Rf value of 0.55 and having an antioxidant activity. The detection of the Q-1047H-R-A substance was performed by means of a thin layer chromatography using a silica gel $60F_{254}$ TLC plate (Merck) and a chloroform-methanol (5:1, v/v) as a developing solvent. Crystallization of this colorless microcrystalline powder from a mixed solvent composed of ethyl acetate and methanol gave Q-1047H-R-A substance as a colorless crystalline powder.

Example 7

To a solution of 500 mg of Q-1047R-A substance in 200 ml of ethyl acetate was added 50 ml of 2% ferric chloride solution, and the mixture was stirred thoroughly in a separating funnel. The ethyl acetate layer obtained was washed with two 50-ml portions of water, anhydrous sodium sulfate was added to the mixture, and dehydration was effected thoroughly. The thus-dehydrated ethyl acetate layer was concentrated to dryness under reduced pressure to give 400 mg of a yellow powder. This yellow powder was dissolved in a small amount of ethyl acetate, and the solution was applied stripwise to a silica gel $60F_{254}$ TLC plate (Merck). This silica gel plate was developed using chloroform-methanol (9:1, v/v) as the developing solvent. Q-1047-A substance showing an Rf value of 0.72 and an SOD-like activity was detected under irradiation with an ultraviolet lamp (254 nm). The silica gel portion containing Q-1047-A substance alone was collected by scratching and packed into a column. Q-1047-A substance was eluted with a chloroform-methanol (9:1, v/v) mixture. The eluate was concentrated to dryness under reduced pressure to give 230 mg of pure Q-1047-A substance as a yellow microcrystalline powder.

Example 8

To a solution of 600 mg of Q-1047H-R-A substance in 200 ml of ethyl acetate was added 50 ml of 2% ferric chloride solution, and the mixture was stirred thoroughly in a separating funnel. The ethyl acetate layer obtained was washed with two 50-ml portions of water, dehydrated over anhydrous sodium sulfate, and concentrated to dryness under reduced pressure to give 480 mg of a yellow powder. This yellow powder was dissolved in a small amount of ethyl acetate, and the solution was applied stripwise to a silica gel $60F_{254}$ TLC plate (Merck). This silica gel plate was developed with chloroform-methanol (9:1, v/v) mixture, and Q-1047H-A-A substance showing an Rf value of 0.73 and an SOD-like activity was detected under irradiation with an ultraviolet lamp (254 nm). The silica gel portion containing Q-1047H-A-A substance alone was collected by scratching and packed into a column. Q-1047H-A-A substance was eluted with a chloroform-methanol (9:1, v/v) mixture. The eluate was concentrated to dryness under reduced pressure to give 280 mg of pure Q-1047H-A-A substance as a yellow microcrystalline powder.

While the invention has been described in detail and with reference to specific embodiments thereof, it will be apparent to one skilled in the art that various changes and modifications can be made therein without departing from the spirit and scope thereof.

What is claimed is:

1. A Q-1047 substance of the general formula (I):

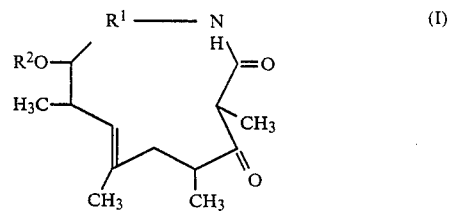

wherein $R^1$ is a group of the formula

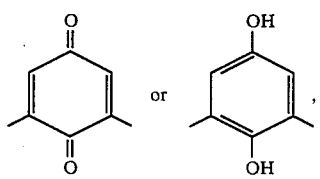 or and R² is a hydrogen atom or a group of the formula

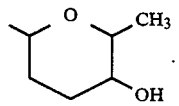

2. A method of producing a Q-1047 substance of the general formula:

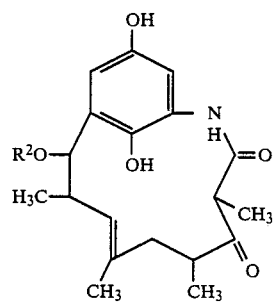

wherein R² is a hydrogen atom or a group of the formula

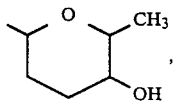

which comprises reducing a compound of the general formula:

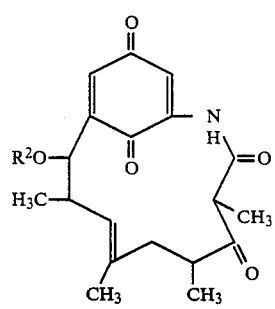

wherein R² is as defined above.

3. A method of producing a Q-1047 substance of the general formula:

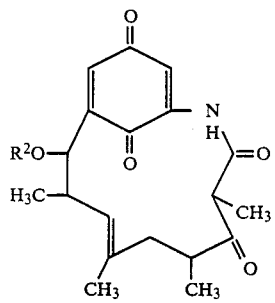

wherein R² is a hydrogen atom or a group of the formula

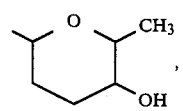

which comprises oxidizing a compound of the general formula:

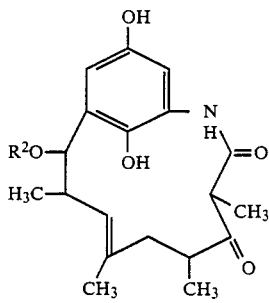

wherein R² is as defined above.

4. A method of producing a Q-1047H substance of the general formula ($I_2$):

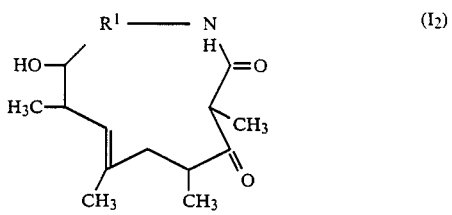

wherein R¹ is a group of the formula

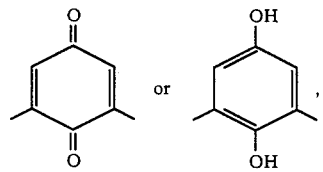

which comprises hydrolyzing a compound of the general formula ($I_1$):

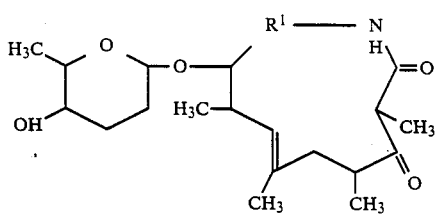

wherein R¹ is as defined above.

* * * * *